(12) United States Patent
Srocka (10) Patent No.: US 9,176,070 B2
(45) Date of Patent: Nov. 3, 2015

(54) INSPECTION ASSEMBLY (71) Applicant: HSEB Dresden GmbH, Berlin (DE)

(72) Inventor: Bernd Srocka, Berlin (DE)

(73) Assignee: HSEB Dresden GmbH, Dresden (DE)

( * ) Notice: Subject to any disclaimer, the term of this patent is extended or adjusted under 35 U.S.C. 154(b) by 4 days.

(21) Appl. No.: 14/246,953

(22) Filed: Apr. 7, 2014

(65) Prior Publication Data

US 2015/0285745 A1 Oct. 8, 2015

(51) Int. Cl.
*G01N 21/00* (2006.01)
*G01N 21/88* (2006.01)
*G01N 21/95* (2006.01)

(52) U.S. Cl.
CPC ........ *G01N 21/8851* (2013.01); *G01N 21/9501* (2013.01); *G01N 2201/062* (2013.01); *G01N 2201/12* (2013.01)

(58) Field of Classification Search
CPC ............ G01N 21/9501; G01N 21/956; G01N 21/95607; G01N 21/94; G01N 21/8806
USPC ....................................... 356/237.5
See application file for complete search history.

(56) References Cited

U.S. PATENT DOCUMENTS

| | | | |
|---|---|---|---|
| 4,922,337 A | 5/1990 | Hunt et al. | |
| 5,298,963 A | 3/1994 | Moriya et al. | |
| 6,324,298 B1 | 11/2001 | O'dell et al. | |
| 6,791,680 B1 | 9/2004 | Rosengaus et al. | |
| 2003/0117596 A1* | 6/2003 | Nishi | 355/51 |
| 2009/0211604 A1* | 8/2009 | Winter et al. | 134/18 |
| 2011/0069507 A1 | 3/2011 | Haugan et al. | |
| 2011/0069878 A1 | 3/2011 | Case et al. | |
| 2011/0102575 A1 | 5/2011 | Case et al. | |

FOREIGN PATENT DOCUMENTS

| | | |
|---|---|---|
| EP | 0 352 797 A2 | 7/1989 |
| EP | 0 352 797 A3 | 7/1989 |
| WO | WO 2009/121628 A2 | 10/2009 |

* cited by examiner

*Primary Examiner* — Tarifur Chowdhury
*Assistant Examiner* — M D Rahman
(74) *Attorney, Agent, or Firm* — Thorpe North & Western, LLP (57) ABSTRACT A method for inspecting wafers or other flat objects having an object surface, comprises the steps of: providing a camera assembly with a camera for recording images of said object surface or portions of said object surface during an exposure time which is limited by a shutter; generating a continuous relative movement of said camera assembly and said object without interruption, whereby a movement blur of said image during said exposure time is caused; continuously illuminating said object with an illuminance which is controlled to remain at the same value; and recording one or more images of at least one of said portions of said object surface with said camera; defining a movement blur which is acceptable for an analysis of said image wherein said exposure time is smaller than a time causing said acceptable movement blur; and performing said analysis of said image.

13 Claims, 6 Drawing Sheets

INSPECTION ASSEMBLY

TECHNICAL FIELD

The invention relates to an assembly for inspecting wafers or other flat objects, comprising:
an object carrier for receiving one of said objects;
a camera assembly with a camera having a plurality of detector elements for taking an image of at least a portion of said object;
a driving assembly for generating a relative movement between the camera assembly and
said object; and
an illumination assembly for illuminating said object.

Furthermore, the invention relates to a method for the inspection of wafers or other flat objects, comprising the steps of:
generating a relative movement of a camera assembly with a camera and the object, where a portion of the object surface is detected by the camera during a recording time;
illuminating the object; and
recording one or more images of at least a portion of the object surface with the camera in the camera assembly.

In different industries flat objects are inspected with optical imaging method regarding the presence of defects. In the semiconductor- and solar cell industry these are, amongst others, wafers. Wafers are discs of semiconductor-, glass-, sheet- or ceramic materials. In certain applications the wafers are typically inspected over the entire surface or at least over large portions thereof. The inspection is called macro-inspection. The lateral resolution required for the recognition of the relevant defects increases with the improvement of the general production technology. Typically, resolutions of 5 microns and smaller—down to 1 micron—are required for new technologies in macro inspection. At the same time devices with a high rate of inspected wafers is desired. Also, it is desired to increase the rate of inspection only by adjusting software parameters while compromising the resolution requirements.

Analogue tasks must be performed in different industries. Displays in production must be inspected for defects in flat-panel industries. Imaging methods for overall inspection of displays are used to discover defects. In the electro industry defects on circuit boards are determined with optical methods in a series of objects.

All applications have the need for quick inspection of a high number of usually similar sample objects. Such objects are circuit boards, wafers, solar cells, displays and the like. They all use sensors for the generation of large images of the sample objects. The images can be generated with optical imaging systems depending on the inspected defects. Optical imaging systems are, for example, detector arrays or line detectors with a plurality of detector elements, also called "pixels".

Usually, the inspected wafers are imaged by taking many individual images after wafer and camera assembly are shifted against each other for each individual image in order to inspect the entire wafer surface. Two-dimensional detector arrays and one-dimensional line detectors can be used as sensor.

The shift between the object and the camera system is either step-wise or continuously. The step-wise shift is effected by moving either the wafer or the camera or both and stopping it for taking the image. Such a system is relatively slow and the rate of inspected objects is limited.

In assemblies with a continuous movement the images are taken during the movement of the wafer without stopping with illumination by sufficiently short flashes. Different resolutions are obtained by using different objectives with different enlargement factors. All such methods have in common that the inspection of an entire wafer requires many images and a mechanical movement. Therefore, the inspection takes considerable time. The inspection time increases by square with increasing resolution.

PRIOR ART

WO 2009 121628 A2 discloses a method for inspection of an entire wafer with one image without moving the wafer. The solution is very fast but compromises the resolution for detecting individual small defects.

US 2011 0069878 A1 shows a two-dimensional camera array arranged above a circuit board moving without interruption.

U.S. Pat. No. 6,791,680 B1 discloses an inspection assembly with an assembly of simple inspection devices simultaneously inspecting the wafer surface. Each of the devices takes an image of a portion of the wafer surface. Furthermore, it is provided that the wafer or the assembly is moved whereby the entire wafer surface can be imaged.

U.S. Pat. No. 5,298,963 and U.S. Pat. No. 6,324,298 disclose devices where the illumination is effected with flashes in order to obtain a still and thereby unblurred image of the object while the object is continuously moved below the camera. The use of flashes has the disadvantage that the intensity varies from flash to flash. The dynamic range of the detector elements of the camera may not be sufficient for such an application. Furthermore it is difficult to generate stable flashes with high frequency and always the same intensity. Accordingly, the moving velocity of the object during imaging is limited.

DISCLOSURE OF THE INVENTION

It is an object of the invention to provide an assembly of the above mentioned kind which enables the inspection of an object in shorter time with high resolution.

According to an aspect of the invention this object is achieved in that
the illumination assembly continuously illuminates the object,
means are provided for controlling the illuminance at a constant value,
the relative movement of the camera assembly and the object is continuous and without interruption, and
a shutter is provided for limiting the exposure time of the imaging of the image, wherein
the exposure time set at the shutter is smaller than the time causing a movement blur of the image which is not worse than acceptable for the evaluation of the image.

In such an assembly the object and/or the camera move without stopping. Thereby, a high inspection rate is achieved. A continuously emitting light source is used which can be controlled to a constant intensity value. By using a shutter the object is continuously illuminated, the sensor, however, is only exposed for a very short time. With such two measures it is ensured that the detector elements of the sensor always operate within their dynamic range even with high inspection rates. Furthermore, the maximum image blur due to the movement of the object can be controlled by setting the opening time of the shutter, i.e. the exposure time of the sensor.

The terms "illumination time" and "illumination duration" designate the time of illumination of the object by the light source. The time, where the shutter of the camera is opened and the camera is actually collecting light is designated with the terms "exposure time" or "exposure duration". The term "recording time" and "recording duration" designates the case where both options are considered at the same time.

Contrary to the use of a flashing light as known from the prior art assemblies the light source used with the present invention can be well controlled. With high speed recordings with detector arrays flashes having an high peak intensity are necessary in order to achieve the same average intensity at the sensor with shorter illumination time and higher frequencies. Such flashes are unstable. Also, problems with providing energy to the flash system are avoided with the present invention. The use of a continuous light source as provided by the present invention enables the stabilization of the light intensity.

A continuous light source can be precisely controlled in known manner by closed-loop-control and thereby stabilized. Such a control also enables the compensation of effects such as temperature drift, aging of the lighting means or warm-up variations which is very difficult if flashes with the required short flash duration are used.

A maximum admissible blur of the image is defined by the image analysis according to the inspection task. It is with otherwise perfect conditions an unavoidable portion of such blur the blur—smear—caused by the movement of the object during the recording time. It is designated here with "movement blur". The movement blur is caused by the simultaneous relative movement between camera and object during the recording time. Generally, the maximum movement blur at a given movement velocity defines a maximum recording time for an image. It is irrelevant how such recording time is limited. The recording time can be limited by the illumination time, such as by using flashing light. In the present invention however, the recording time is limited by the exposure time corresponding to the shutter opening time of the camera. By limiting the exposure time it is ensured that the element limiting the recording time generates the same recording time for each image with high reproducibility.

If the movement blur exceeds the amount admissible for the further analysis, known mathematical methods can be applied to calculate a focused image. A Wiener deconvolution (see e.g. http://en.wikipedia.org/wiki/Wiener_deconvolution) can be used for this purpose. The method is named after Norbert Wiener and is based on a Fourier-transformation of the image and unfolding the image from the momentum response function of the recording system in the Fourier space.

If a sufficiently large edge range of a first image of a series of images has a well known signal value the movement blur can be removed by calculation according to a simple difference method. Such a well known signal value can be, for example, zero for the edge portion which remains without illumination or has no reflecting object portion.

Preferably, it is provided that the camera is a detector array with detector elements arranged in lines and columns. However, a line-detector may also be used, where all detector elements are arranged in one line.

In a modification of the invention it is provided that the exposure time set at the shutter is smaller than the time necessary for shifting the object and the camera in a relative movement for less than 5 lengths of the area imaged on one detector element, preferably less than twice the length of the area imaged on one detector element and even more preferably less than one length of the area imaged on one detector element. In a further modification of the invention it is provided that the exposure time set at the shutter is smaller than the time necessary for shifting the object and the camera in a relative movement for less than half the length of the area imaged on one detector element.

In a preferred embodiment of the invention the shutter is an electronically implemented global shutter with charge transfer in a CMOS image sensor or in a CCD image sensor or any other electronic shutter.

A method according to the present invention provides that the exposure time set at the shutter is smaller than the time necessary for shifting the object and the camera in a relative movement for less than half the length of the area imaged on one detector element. Such limitation is sufficient for many applications. Depending on the velocity of the components, however, the time may be shorter.

In an advantageous embodiment of the invention the continuous illumination is interrupted between the image recordings while the illumination duration remains a multitude of the exposure time set at the shutter. Such an interruption prevents overheating and aging of the illumination components and saves energy. There is, however, no influence of such interruptions on the imaging.

In a further modification of the invention it is provided that the recorded images overlap in overlapping ranges. This means that each object portion is imaged twice or even more times. In such a case it can be provided that the signal values at detector elements belonging to the same coordinates in the overlapping ranges of the object are used for the calculation in order to improve the signal-to-noise ratio by adding up the signal values of the respective detector elements. Alternatively, it can be provided that the signal values at detector elements belonging to the same coordinates in the overlapping ranges of the object are used for the calculation in order to improve the signal-to-noise ratio by calculating the average or median value of the signal values of the respective detector elements. Doubly imaged portions are, therefore, not just discarded but included in the calculation. Thereby, the signal-to-noise ratio is improved in the overlapping ranges.

Preferably, the images overlap so far, that the series of images taken of the object enable the generation of at least two overall images covering the object surface without gaps, and wherein each of the individual images is used exactly in one of the overall images and none of the individual images is used in both of the at least two overall images.

Furthermore, it can be provided that the images for the overall images are taken with different illuminating conditions and wherein the images having the same illuminating conditions are assembled to an overall image. Such different illumination conditions are in particular bright field illumination and dark field illumination, illumination with different colors, i.e. wavelengths in the visible wavelength range or illumination with light in the visible and infrared wavelength ranges.

A method according to an aspect of the invention can comprise the steps of:
A method for inspecting wafers or other flat objects having an object surface, comprising the steps of:
  providing a camera assembly with a camera for recording images of said object surface or portions of said object surface during an exposure time which is limited by a shutter;
  generating a continuous relative movement of said camera assembly and said object without interruption, whereby a movement blur of said image during said exposure time is caused;
  continuously illuminating said object with an illuminance which is controlled to remain at the same value; and recording one or more images of at least one of said portions of said object surface with said camera;

wherein using mathematical methods and a velocity of said relative movement an image with decreased blur is generated from a recorded image which has a movement blur.

The assembly and the method of the invention is described below using a wafer as an example. Obviously, the assembly and the method can, however, also be used for any other flat sample object.

Further modifications of the invention are subject matter of the subclaims. A preferred embodiment is described below in greater detail with reference to the accompanying drawings.

DESCRIPTION OF THE EMBODIMENT

The embodiment uses an inspection assembly having a well-known set-up. Wafers are consecutively moved below a camera. In the present embodiment the camera is stationary and the objects are moved below the camera. The movement between the camera and the object is continuous. This means that the camera does not have a fixed position above an object point at any recording-time.

Figure 1:
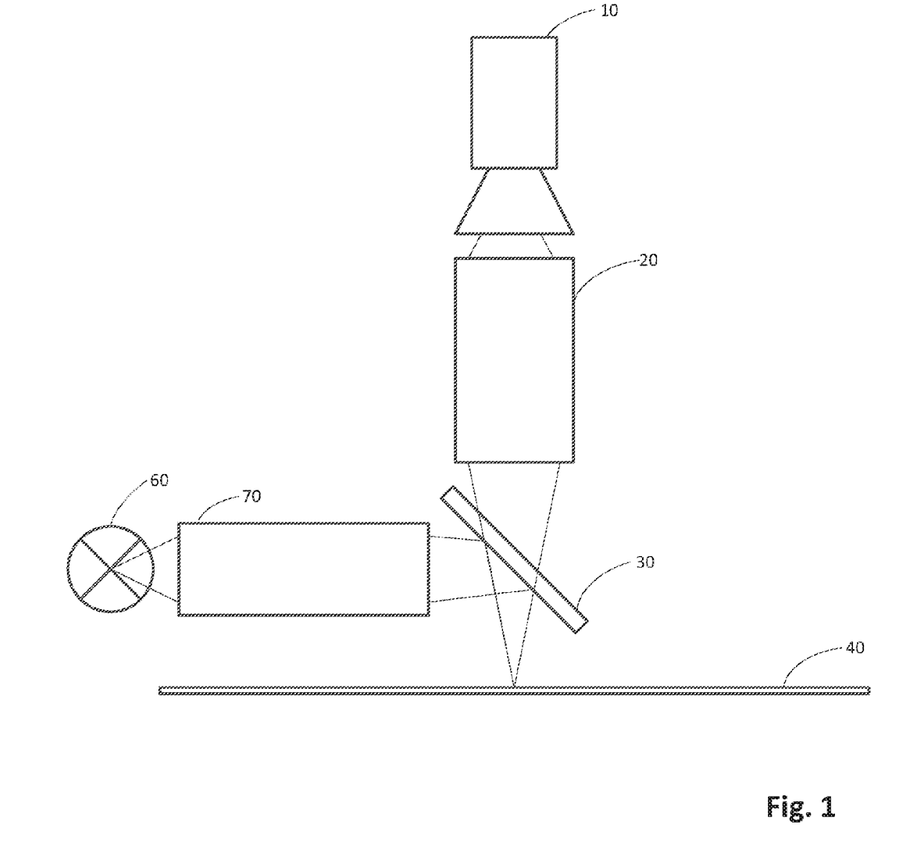
FIG. 1 schematically illustrates the set-up of an inspection assembly with a detector array.

FIG. 1 shows an embodiment with a detector array camera with a sensor comprising detector elements arranged in lines and columns. The object is continuously illuminated by a light source 60. A control loop is provided for controlling the intensity to a constant value. The light is transferred by homogenization means 70 for transferring and homogenizing the illumination of the field of view. Homogenization means 70 contain optical rods and lens systems to support illumination homogeneity. In the present embodiment the homogenization is achieved by passing the light through a hexagonal glass rod and transferring it to the objective via a glass fiber bundle. The light is directed to the sample location by a semi-transparent mirror 30 for illumination. The light is reflected by the sample 40 and a portion thereof passes through the semi-transparent mirror 30 in order to be imaged by an imaging optics 20 to the camera 10. In the present embodiment the camera is provided with a global shutter. This enables to limit the exposure time of the sensor comprised in the camera to a desired value.

Figure 2:
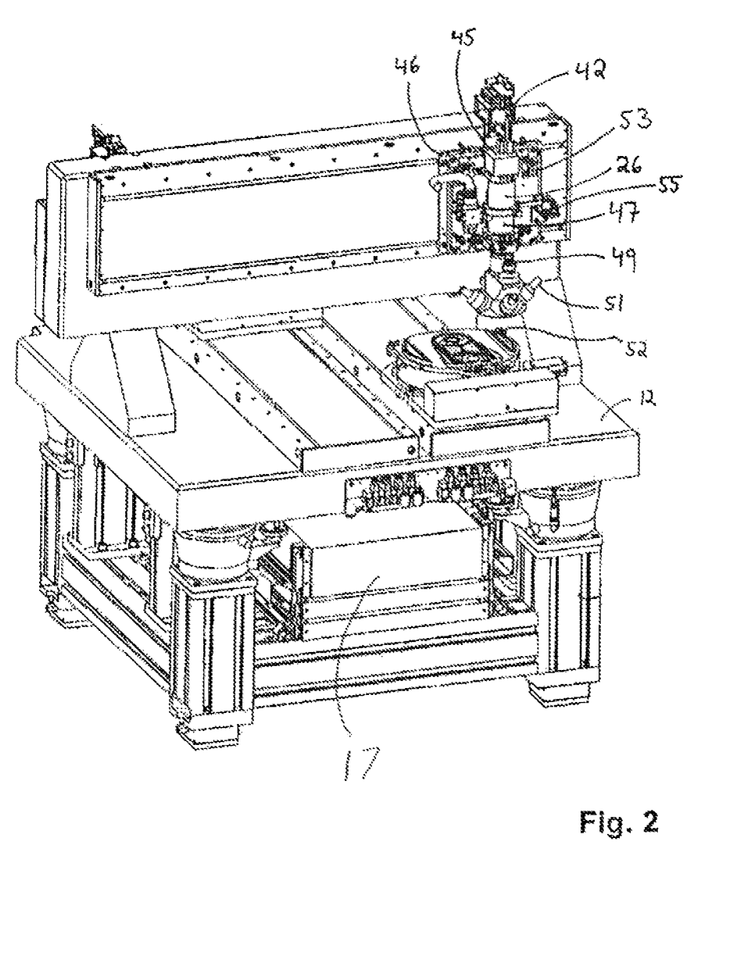
FIG. 2 shows the set-up of FIG. 1 in greater detail.

FIG. 2 is a more detailed representation of the assembly of FIG. 1. Numeral 12 designates a base plate for mounting the inspection unit. Numeral 52 designates a moveable carrier device for receiving a wafer. A moveable slide 46 carries the camera unit. The camera unit 42 comprises the camera 45, optical elements 26 and 47 for imaging the inspected sample location under the sensor of the camera and adjusting means 53 and 55. Numeral 26 denotes the tubus lenses and 47 the front lens of the objective, while 53 is an adjustable fixture to adjust the height and tilt of the objektiv-camera system. Numeral 55 designates a fine tune element for the rotational adjustment to make sure that the images are with their long side orthogonal to the scan direction. The light is reflected into the optical path by means of a mirror 49. An additional light source is provided for dark field illumination. This light is reflected into the optical path by an optical element 51 holding four light guide fiber bundles and for each fiber a set of lenses for the proper illumination of the field of view. The additional illumination has a non-perpendicular angle of incidence. LED-light sources and a fiber unit for transferring the light are provided for this purpose.

The sensor of the camera 10 comprises a plurality of detector elements for generating signals. The signals of the detector elements of one image are combined with signals of the detector elements of further images to an overall image. It is, however, not necessary to always consider the entire object. It may be sufficient to image and evaluate interesting portions of the object.

The recording time is limited in the present embodiment by the exposure time of the camera, i.e., the duration of the opening of the shutter. The illumination time of the light source exceeds the exposure time at least in so far as it will not have any influence on the resulting movement blur. If the movement blur limited by the exposure time still exceeds the amount admissible for the further analysis, a focused image can be obtained mathematically according to suitable methods described below.

Figure 3:
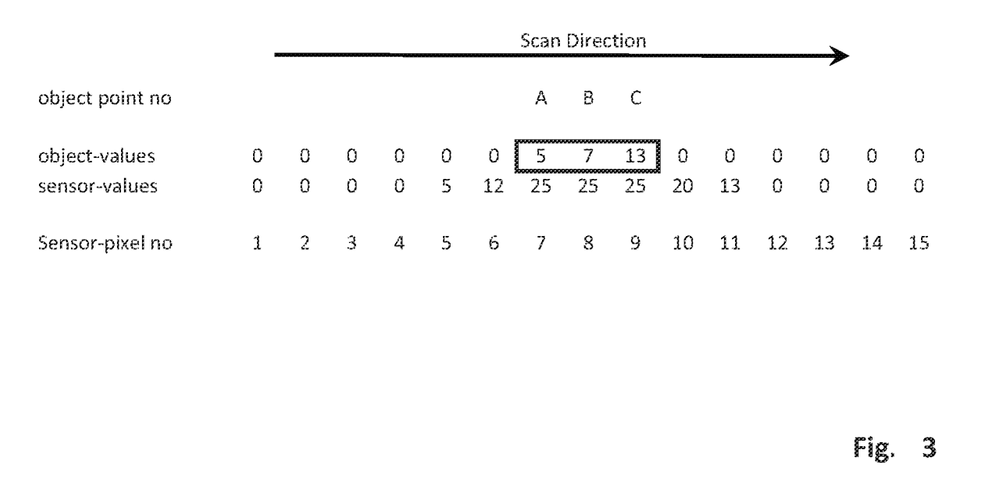
FIG. 3 schematically illustrates a section of a detector line and the object values measured for this section.

The calculation of a focused image from a movement blur with a simple difference method is illustrated in FIG. 3. It can be used if a sufficiently large edge portion of the first image of a series of images has a well defined, known signal value. Such a well defined signal value can be, for example, zero for an edge portion where there is no illumination and which does not image a reflecting object.

FIG. 3 shows three object points A, B and C. The detector elements of one line of the sensor are numbered consecutively with numbers 1 to 15. They are indicated in the lowest line in FIG. 1. Obviously, typical commercially available sensors have many more detector elements in one line, such as, for example, 512 or 1024 detector elements. The smaller number was chosen in the present illustrated embodiment only to provide a better understanding.

Each point on the object has a certain brightness value. If the point is detected with a detector element a signal is generated by the detector element. The signal depends on the brightness value of the object. Additionally, the signal is influenced by further factors. In the present case by the relative movement between camera and object.

In the example shown in FIG. 3 the object moves five detector elements relative to the sensor of the camera during the exposure time. In this case the light reflected from object point A in FIG. 3 is distributed over five detector elements numbered 5 to 9 while the light reflected from object point B is distributed over the five detector elements numbered 6 to 10. The light reflected from object point C is distributed over the five detector elements numbered 7 to 11, and so on.

It can be seen from FIG. 3 that re-calculation can be effected by simple difference methods if it is ensured that detector elements 1 to 5, for example, are always without any signal, hence zero, respectively, some dark noise level of the sensor. For instance, in the example of FIG. 3 the signal is smeared over 5 detector elements. In a proportional manner the object signal value S of an object element n equals the term $S=s(n-2)-[s(n-3)+s(n-4)+s(n-5)+s(n-6)]$, where $s(x)$ is the signal value of the sensor detector element number x. Therefore, in the example of FIG. 3, the object value of object element B corresponding to object element no. 8 equals the $s(6)-[s(5)+s(4)+s(3)+s(2)]=12-[5+0+0+0]=7$.

The illumination can be effected with a continuously emitting light source. However, it is also possible to use a pulsed or interrupted light source instead of a continuously emitting light source. As an example, the present embodiment uses a LED light source. Obviously, any other kind of light source may also be used. If a LED light source is used the intensity can be increased up to ten-times the intensity by short current pulses. The light intensity which can be achieved in such a way has a high importance for the detection because the short exposure time requires a very high intensity. Such a current control is commercially available by, for example, Gardasoft. The short pulses of the LED source require sufficient time for cooling down the component by switching off in-between pulses. The illumination time is, however, much longer than the exposure time of the sensor. The ratio between the illumination time where the light source is switched on and the cooling time is commonly known as duty cycle. A duty cycle of at least 1:100 is necessary for a control as used in the present embodiment. The illumination time is still much longer than the exposure time of the sensor with opened shutter. The condition is easily met. If, for example, recording time of 4 microseconds is required with a relative velocity between object and camera of 400 mm/s the time between two images is 24,996 ms with a field of view of the sensor in the direction of the movement which is, for example, 10 mm. The length of the pulse of the illumination can be set to, for example, 100 microseconds corresponding to a duty cycle of the light source of 1:250. Since the pulse length of the light source in this example is still 25-times as much as the recording time the blur of the image is only determined by the exposure time of the camera and not influenced by the illumination time by the interrupted light from the light source. For purposes of the invention and of this disclosure, this is still considered as continuously illuminating the object. The important thing is that the object is illuminated continuously during at least the entire exposure time. Therefore, the light source has no influence on the movement blur.

Figure 4:
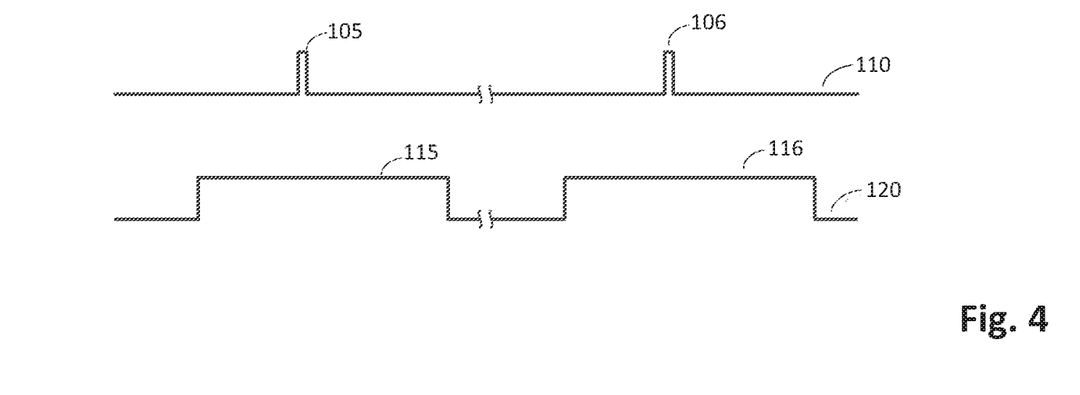
FIG. 4 schematically illustrates the ratio between the exposure time and the illumination time.

The method is illustrated in FIG. 4. The time beam 110 of the camera shows two exposure times (shutter opening times) 105 and 106. They determine the length of the remaining movement blur of the image. The time beam of the light source 120 shows the corresponding illuminating times. They are the pulse 115 for the image 105 and the pulse 116 for the image 106. The light source has no influence on the movement blur due to the long duration of the switched-on-phases and, therefore, cannot generate a quasi stationary image. Both time beams are interrupted for better understanding of the conditions which is why the duty cycle conditions are not shown to scale.

The assembly can generate an overall image by consecutive imaging and assembly of adjacent object portions. In the present embodiment several images of the object are taken which are shifted in time and have a spatial overlap. For example, two, three or even more shifted images are generated with a sufficiently fast camera. The frequency of the imaging is multiplied. This is illustrated below in greater detail by way of example. Three shifted images are taken under the conditions described in the example above, i.e. 4 microseconds exposure time (shutter opening time), 40 microseconds illumination time and an image taking frequency of 120 fps (frames per second). The duty cycle for the illumination is 1:208 and the illumination time is 10-times as long as the recording time. Accordingly, the blur is determined by the exposure time.

Figure 5:
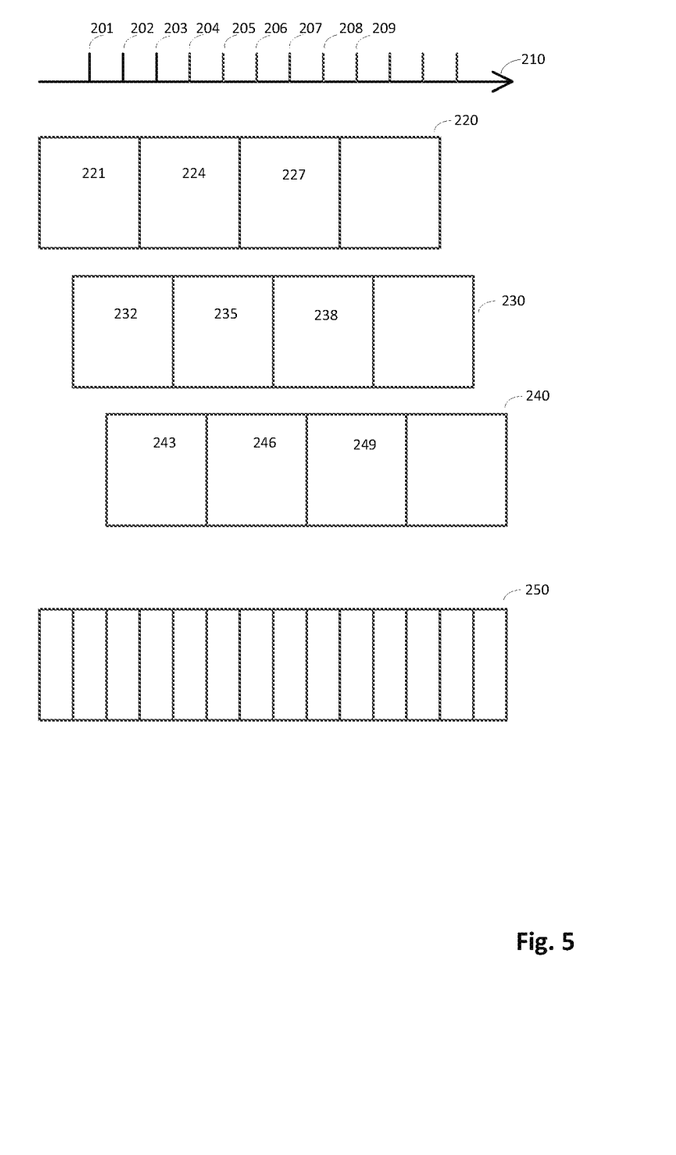
FIG. 5 illustrates the inspection of objects with overlapping images.

This method is illustrated in FIG. 5. Numeral 210 designates the time and at the same time the moving direction of the wafer relative to the camera assembly. Lines 201, 202, 203, 204, . . . to 209 represent the times where an image taking procedure is started. The three image series 220, 230 and 240 are time-shifted, spatially overlapping image series. They are shifted orthogonally to the direction of the movement and thereby shown separately in order to provide a better overview. In the real embodiment they are positioned on exactly the same movement trajectory as the line 250. Image 221 is taken at time 201, image 232 is taken at time 202 and image 243 is taken at time 203. This is continued whereby images 221, 224 and 227 are generated at times 201, 204 and 207. Correspondingly images 232, 235 and 238 are generated at times 202, 205 and 208, respectively, and images 243, 246 and 249 are generated at times 203, 206 and 209. In such a way the entire object can be imaged in traces and finally in the form of a meander. An overall image of the object can be assembled from the image series 220, 230 and 240.

The three overall images can be used in different ways. First of all, they can be used for improving the signal-to-noise ratio of the inspection. Assuming, that the optical shift of the images is small compared to the desired resolution the images can be all taken into account by calculation. This can be effected by, for example, forming the average value or the median for each image point.

Figure 6:
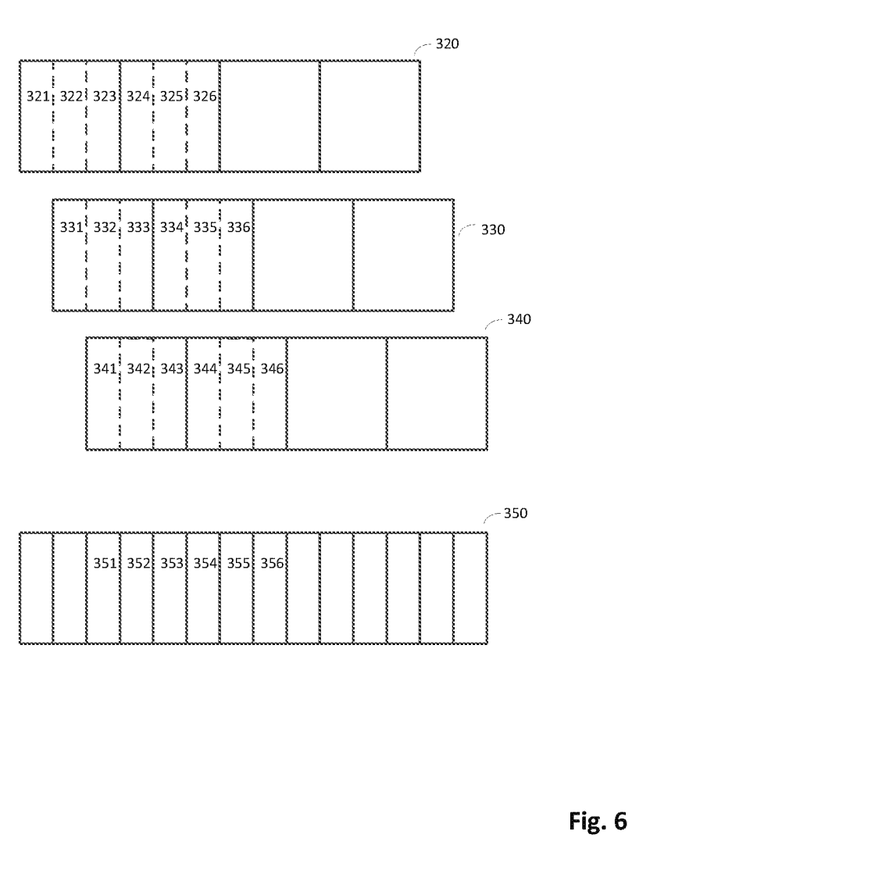
FIG. 6 illustrates the inspection of objects with overlapping images with different illumination conditions.

This proceeding is illustrated in FIG. 6. The three image series 320, 330, 340 are shifted in time and have a spatial overlap. Again, they are shifted for better overview of the moving direction and thereby shown separately. In the real embodiment they are on the same movement trajectory as the series 350. If three image series 320, 330 and 340 are used to improve the signal-to-noise ratio of the overall image, one single overall image 350 of the object is generated by calculating the result from the three partial image series 320, 330 and 340. This is effected in a simple way by adding up. The subsection 352 of the overall image 350 is generated by adding up the grey values of the detector elements 324, 333 and 342 and the subsection 353 from the detector elements 325, 334 and 343, and so on. The sum is taken element wise, i.e. the signal values of each detector element, for example the signal value from detector element 323, is added to the signal values from the corresponding detector elements in the corresponding partial image series, for example detector elements 332 and 341, to obtain the overall image subsection 351. The calculation mathematically corresponds to the forming of an average and the higher dynamical range generated by simple addition rather than forming a true average can be advantageously used for further analysis. However, different combination methods may be used, such as, for example, a median of the grey values of corresponding detector elements. In such a way an improved overall image 350 of the object can be generated from the three image series 320, 330 and 340.

Furthermore, the present embodiment enables the combination of three shifted images with different illumination kinds. For example, the generation of three image portions is possible in three different colors of light, such as red, green and blue. This enables a fully covering true color image for the entire object image having a resolution corresponding to the maximum possible resolution of the sensor used in the assembly. Such a true color image is more advantageous for inspection purposes than a colored image generated by the use of filter techniques, such as a Bayer-Filter, in front of the camera sensor. The original image data of the detector elements are distributed to the individual colors in the image generated by using a Bayer-Filter. Two of each four detector elements are provided with a green filter and each of the remaining detector elements is provided with a red filter and a blue filter, respectively. The color values for further colors are generated by interpolation of adjacent elements. Such an interpolation is obviously less accurate than a true 3-color image and it can happen that small colored defects are overseen. With the present method such errors are avoided. The three image series 220, 230 and 240 shown in FIG. 5 are each assembled to an overall image of the object. From the image series 220 a green overall image of the object is obtained, from the image series 230 a blue overall image of the object is obtained and from the image series 240 a red overall image of the object is obtained if green light was used for illumination at times 201, 204 and 207, blue light was used for illumination at times 202, 205 and 208 and red light was used for illumination at times 203, 206 and 209. Such colored overall images are only spatially shifted relative to each other. The shift is known, however, whereby the shift can be appropriately considered in the subsequent analysis of the three colored overall images.

The present embodiment has been described in great detail with reference to specific set-ups and components. While this embodiment was described for better understanding of the invention it is not meant in any way to limit the scope of the present invention. Various modifications and alterations can be carried out which are obvious for the person skilled in the art once he learnt about the invention. For example, it is possible to move the camera rather than the object or both. Such relative movement can be effected by both the camera and the object, where, for example, the camera carries out the movement in one direction and the object is moved in a perpendicular direction. It does not matter if the object or the camera or both are moved. Only the relative movement of the two is important. Also, the invention does not depend on the kind of sensor used in the camera. While a detector array with detector elements has some advantages a line camera may also be used which has different advantages.

Further modifications of the inventive idea use different illumination combinations. Bright field- and dark field illumination can be used. For bright field illumination light is incident on the object surface with a steep angle, which is nearly perpendicular to the surface. For dark field illumination light is incident on the surface under a small angle relative to the surface. Also, different wavelengths or wavelength ranges can be used as illumination. Visible light, for example, can be combined with light in the near Infrared region and the like.

What is claimed is:

1. An assembly for inspecting wafers or other flat objects, each of said objects having
    an object surface, the assembly comprising
    an object carrier for receiving one of said objects;
    a camera assembly with a camera having a plurality of detector elements for taking an image of at least a portion of said object surface during an exposure time;
    a driving assembly for generating a continuous relative movement without interruption between said camera assembly and said object wherein said relative movement causes a movement blur of said image during said exposure time;
    an illumination assembly for continuously illuminating said object, means controlling said illuminance at a constant value,
    a shutter for limiting said exposure time,
    means for performing an analysis of said image are provided, said means defining a movement blur which is acceptable for said analysis of said image;
    wherein said exposure time is smaller than a time causing said acceptable movement blur, and
    wherein an area is attributed to each of said detector elements which is a portion of said object surface imaged on said detector element and wherein said exposure time is smaller than a time necessary for said relative movement along less than 5 lengths of said area imaged on one of said detector elements, preferably less than twice of said length of said area imaged on one of said detector elements and even more preferably less than one length of said area imaged on one of said detector elements.

2. The assembly of claim 1, and wherein said camera is a detector array with detector elements arranged in lines and columns.

3. The assembly of claim 1, and wherein said exposure time is smaller than a time necessary for said relative movement along less than half a length of said area imaged on one of said detector elements.

4. The assembly of claim 1, and wherein said camera assembly comprises a CMOS image sensor or a CCD image sensor and said shutter is a global shutter with charge transfer or any other electronic shutter.

5. A method for inspecting wafers or other flat objects having an object surface, comprising the steps of:
    providing a camera assembly with a camera for recording images of said object surface or portions of said object surface during an exposure time which is limited by a shutter;
    generating a continuous relative movement of said camera assembly and said object without interruption, whereby a movement blur of said image during said exposure time is caused;
    continuously illuminating said object with an illuminance which is controlled to remain at the same value; and
    recording one or more images of at least one of said portions of said object surface with said camera;
    defining a movement blur which is acceptable for an analysis of said image wherein said exposure time is smaller than a time causing said acceptable movement blur; and
    performing said analysis of said image, and
    wherein an area is attributed to each of said detector elements which is a portion of said object surface imaged on said detector element and wherein said exposure time is smaller than a time necessary for said relative movement along less than 5 lengths of said area imaged on one of said detector elements, preferably less than twice of said length of said area imaged on one of said detector elements and even more preferably less than one length of said area imaged on one of said detector elements.

6. The method of claim 5, and wherein said exposure time is smaller than a time necessary for said relative movement along less than half a length of said area imaged on one of said detector elements.

7. The method of claim 5, and wherein said continuous illumination is interrupted between said image recording and said object is illuminated many times of said exposure time.

8. The method of claim 5, and wherein said recorded images overlap in overlapping ranges.

9. The method of claim 5, and wherein said detector elements generate signal values corresponding to the illuminance of said detector element and said signal values belonging to said areas in said overlapping ranges of said object are used for a calculation in order to improve a signal-to-noise ratio of said signal values by adding up said signal values.

10. The method of claim 5, and said detector elements generate signal values corresponding to the illuminance of said detector element and said signal values belonging to said areas in said overlapping ranges of said object are used for a calculation in order to improve a signal-to-noise ratio of said signal values by calculating an average or median value of said signal values.

11. The method of claim 5, and wherein said images overlap so far, that a series of images taken of said object enable a generation of at least two overall images covering said object surface without gaps, and wherein each of said individual images is used exactly in one of said overall images and none of said individual images is used in both of said at least two overall images.

12. The method of claim 11, and wherein said images for said overall images are taken with different illuminating conditions and wherein said images having said same illuminating conditions are assembled to an overall image.

13. A method for inspecting wafers or other flat objects having an object surface, comprising the steps of:
- providing a camera assembly with a camera for recording images of said object surface or portions of said object surface during an exposure time which is limited by a shutter;
- generating a continuous relative movement of said camera assembly and said object without interruption, whereby a movement blur of said image during said exposure time is caused;
- continuously illuminating said object with an illuminance which is controlled to remain at the same value; and
- recording one or more images of at least one of said portions of said object surface with said camera;
- wherein using mathematical methods and a velocity of said relative movement an image with decreased blur is generated from a recorded image which has a movement blur, and
- wherein an area is attributed to each of said detector elements which is a portion of said object surface imaged on said detector element and wherein said exposure time is smaller than a time necessary for said relative movement along less than 5 lengths of said area imaged on one of said detector elements, preferably less than twice of said length of said area imaged on one of said detector elements and even more preferably less than one length of said area imaged on one of said detector elements.

* * * * *